United States Patent [19]

Tinney

[11] 4,022,760
[45] May 10, 1977

[54] TRIPEPTIDES AND METHODS FOR THEIR PRODUCTION

[75] Inventor: Francis John Tinney, Ann Arbor, Mich.

[73] Assignee: Parke, Davis & Company, Detroit, Mich.

[22] Filed: Jan. 19, 1976

[21] Appl. No.: 650,096

[52] U.S. Cl. .............. 260/112.5 LH; 260/112.5 R; 424/177
[51] Int. Cl.² ...................................... C07C 103/52
[58] Field of Search ........... 260/112.5 R, 112.5 LH

[56] References Cited
UNITED STATES PATENTS 3,725,380   4/1973   Konig et al. ................ 260/112.5 R

OTHER PUBLICATIONS

J. M. Stewart and J. D. Young, "Solid Phase Peptide Synthesis," Freeman and Co., San Francisco, 1969, pp. 9–13.
J. D. Roberts and M. C. Caserio, "Basic Principles of Organic Chemistry," Benjamin, Inc., New York, 1965, p. 564.
E. Schroder and K. Lubke, "The Peptides," vol. 1, Academic Press, New York, 1965, pp. 108–111.

*Primary Examiner*—Delbert R. Phillips
*Attorney, Agent, or Firm*—Stephen Raines; George M. Richards; David B. Ehrlinger

[57] ABSTRACT

New tripeptides having the formula A-$R_1$-Tyr(benzyl)-Thr(benzyl)-$R_2$ wherein A is t-butoxycarbonyl or cyclohexylcarbonyl, $R_1$ is Trp, His(benzyl), Cys(benzyl) or Pro and $R_2$ is lower alkoxy, hydrazino, amino, lower alkylamino, di(lower alkyl)amino, benzylamino, allylamino, (diethoxyphosphinyl)methylamino, 2-(diethoxyphosphinyl)ethylamino or 2-[[(phenylmethyl)amino]sulfonyl]ethylamino, methods for their production, and the use of said tripeptides as luteinizing hormone releasing factor antagonists.

2 Claims, No Drawings

TRIPEPTIDES AND METHODS FOR THEIR PRODUCTION

SUMMARY AND DETAILED DESCRIPTION

The present invention relates to new peptide compounds that are useful as luteinizing hormone releasing factor antagonists and to methods for their production. More particularly, the invention relates to new N-protected tripeptides that are represented by the formula

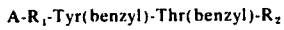

wherein A is t-butoxycarbonyl or cyclohexylcarbonyl, $R_1$ is Trp, His(benzyl), Cys(benzyl) or Pro and $R_2$ is lower alkoxy, hydrazino, amino, lower alkylamino, di(lower alkyl)amino, benzylamino, allylamino, (diethoxyphosphinyl)methylamino, 2-(diethoxyphosphinyl)ethylamino or 2-[[(phenylmethyl)amino]sulfonyl]ethylamino.

In formula I, the conventional symbols for amino acid residues of peptide compounds are used and each is intended to have the following meaning: Trp, L-tryptophyl; His(benzyl), $N^{im}$-benzyl-L-histidyl; Cys(benzyl), S-benzyl-L-cysteinyl; Pro, L-prolyl; Tyr(benzyl), O-benzyl-L-tyrosyl and Thr(benzyl), O-benzyl-L-threonine. In addition, the term "lower alkyl" is intended to mean a straight, branched or cyclic saturated hydrocarbon moiety of up to six carbon atoms, such as methyl, ethyl, isopropyl and cyclopropyl and "lower alkoxy" is intended to mean an alkoxy group having a straight, branched or cyclic saturated hydrocarbon moiety of up to six carbon atoms, such as methoxy, ethoxy and isopropoxy. These symbols and terms will also be used in the formulae that follow other compounds and each such symbol or term should be understood to have the meaning given above.

In accordance with this invention, compounds of the formula I, wherein A and $R_1$ are as previously defined and $R_2$ is lower alkoxy, are produced by removing a protected tripeptide from a resin complex of the following structure

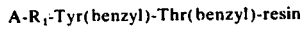

wherein said resin is a resin employed in solid phase peptide syntheses, such as those disclosed in a text by Stewart and Young, "Solid Phase Peptide Synthesis", W. H. Freeman & Company, San Francisco, 1969, which is incorporated by reference, preferably the resin is a cross-linked copolymer comprising 98 to 99 percent polystyrene cross-linked with 1 to 2 percent divinylbenzene, which is attached to the protected tripeptide through a methyleneoxy bridge wherein the methylene group is attached to the polymeric portion of the resin and the oxygen atom is attached to the protected tripeptide and A and $R_1$ are as previously defined; by treating said resin of the formula II with a lower alkyl alcohol in the presence of a tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

While it is not a preferred procedure, compounds of the formula I wherein $R_2$ is hydrazino, amino, lower alkylamino, di(lower alkyl)amino, benzylamino or allylamino may be prepared by reacting compounds of the formula II wherein A and $R_1$ are as previously defined, with hydrazine, ammonia, lower alkylamine, di(lower alkyl)amine, benzylamine or allylamine.

The resin complex is suspended in a solvent, such as methanol, ethanol, dimethylformamide, etc., at a temperature of from about 0° to 50° C. for periods of from 12 hours to 10 days. When employing less reactive amines, the preferred solvent is dimethylformamide.

The complex resins of the formula II are prepared by coupling a protected amino acid of the formula

wherein A and $R_1$ are as previously defined, with a complex resin of the formula

in an organic solvent, such as dichloromethane with the aid of dicyclohexylcarbodiimide. The three components may generally be used in about equimolar quantities, but excess amounts of the protected amino acid of dicyclohexylcarbodiimide are sometimes advantageous. The reaction is generally conducted at about room temperature for a period of from about fifteen minutes to about 16 hours.

The complex resins of the formula IV are prepared by treating complex resins of the formula

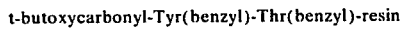

with a large excess of trifluoroacetic acid utilizing dichloromethane as the solvent at temperatures of from 20° to 30° C. for about 10 minutes.

The complex resin of formula V are prepared by coupling

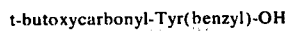

to complex resins of the formula

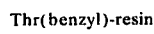

using the reaction procedure described for the preparation of compounds of the formula II.

The complex resins of the formula VI are prepared by treating the known complex resins of the formula

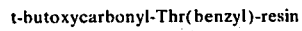

with trifluoroacetic acid using the reaction procedure for the preparation of compounds of the formula IV.

In accordance with this invention, compounds of the formula I, wherein A and $R_1$ are as previously described and $R_2$ is hydrazino, amino, lower alkylamino, di(lower alkyl)amino, benzylamino or allylamino are prepared by reacting a compound of the formula I wherein $R_2$ is alkoxy, preferably methoxy with hydrazine, ammonia, lower alkylamine, di(lower alkyl)amine, benzylamine or allylamine.

The reactions are conducted at temperatures of from about 5° to 100° C. for from 3 hours to four days, preferably about room temperature. Generally, a large excess of hydrazine, preferably used in the form of its hydrate, or amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

In addition, in accordance with this invention, compounds of the formula I, wherein A and $R_1$ are as previously defined and $R_2$ is amino, lower alkylamino, di(lower alkyl)amino, benzylamino, allylamino, (diethoxyphosphinyl)methylamino, 2-(diethoxyphosphinyl)ethylamino or 2-[[(phenylmethyl)amino]sulfonyl]ethylamino are prepared by reacting a compound of the formula

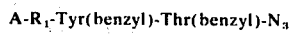
A-$R_1$-Tyr(benzyl)-Thr(benzyl)-$N_3$   VII with ammonia, lower alkylamine, di(lower alkyl)amine, benzylamine, allyl amine, (diethoxyphosphinyl)methylamine, 2-(diethoxyphosphinyl)ethylamine or 2-[[(phenylmethyl)amino]sulfonyl]ethylamine in a non-reactive solvent such as dimethylformamide, dioxane, tetrahydrofuran or mixtures thereof. The reaction is carried out at about −30° to about 0° C. for about 12 to 24 hours, preferably −20° to 0° C. for from 16 to 19 hours. The two reactants are used in approximately equimolar amounts although a slight excess of amine, about 10 percent is preferred. When A is t-butoxycarbonyl, care should be taken to avoid the presence of an excess of acid.

The azide compounds of the formula VII are normally prepared in situ by reacting a peptide hydrazide compound of the formula I wherein A and $R_1$ are as previously defined and $R_2$ is hydrazino, with a lower alkyl nitrite, preferably isoamyl nitrite in the presence of an acid, preferably hydrochloric acid, in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula I. The preparation of the azide is carried out at a temperature between −60° and 10° C. Following the in situ formation of the azide of formula VII and prior to the further reaction of the peptide azide with the appropriate amine to form certain tripeptides of formula I, a tertiary amine such as triethylamine is added to the reaction mixture to neutralize the acid used.

Compounds of the formula I wherein A and $R_1$ are as previously described and $R_2$ is hydrazino, amino, lower alkylamino, di(lower alkyl)amino, benzylamino, allylamino, (diethoxyphosphinyl)methylamino, 2-(diethoxyphosphinyl)ethylamino or 2-[[(phenylmethyl)amino]sulfonyl]ethylamino are prepared by coupling a coupound of the formula

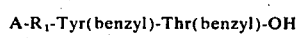
A-$R_1$-Tyr(benzyl)-Thr(benzyl)-OH   VIII with hydrazine, ammonia, lower alkylamine, di(lower alkyl)amine, benzylamine, allylamine, (diethoxyphosphinyl)methylamine, 2-(diethoxyphosphinyl)ethylamine or 2-[[(phenylmethyl)amino]sulfonyl]ethylamine, in an inert solvent in the presence of dicyclohexylcarbodiimide.

The above reaction is carried out using approximately equivalent amounts of reactants and dicyclohexylcarbodiimide in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° to 50° C., preferably room temperature for periods of from 10 hours to 5 days.

1-Hydroxybenzotriazole may also be used in the above reaction in addition to the dicyclohexylcarbodiimide. The 1-hydroxybenzotriazole is added in a ratio of one to two equivalents when compared to the reactants.

The compounds of the formula VIII are prepared by the hydrolysis of a compound of formula I wherein A and $R_1$ are as previously defined and $R_2$ is lower alkoxy. The reaction is conducted at temperatures of from 20° to 30° C. using about 0.25 ml. of a two normal aqueous sodium hydroxide solution and 10 ml. of solvent for each millimole of ester. The compound of formula VIII is isolated after acidification with aqueous citric acid.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Tripeptides of this invention were screened for LRF antagonist activity in vitro using rat anterior pituitary cell cultures as described by Vale et al. [Endocrinology, 91, 562 (1972)]. The inhibition of LRF (luteinizing hormone release factor) induced luteinizing hormone (LH) release into the culture medium is the endpoint in this in vitro bioassay:

Following are the results of the above tests on certain preferred compounds.

| | ACTIVITY TABLE FOR IN VITRO TEST IN RAT ANTERIOR PITUITARY CELL CULTURES | | |
|---|---|---|---|
| | Molar Conc. | LH Value ng/ml. | % LH Release Inhibition |
| $N^\alpha$-t-butoxycarbonyl-$N^{im}$-benzyl-L-histidyl-O-benzyl-L-tyrosyl-O-benzyl-L-threonine methyl ester | 1 × 10⁻⁶ | 20.27 | 59 |
| LRF control | 2.5 × 10⁻¹⁰ | 35.89 | |
| Saline control | | 9.39 | |
| $N^\alpha$-t-butoxycarbonyl-$N^{im}$-benzyl-L-histidyl-O-benzyl-L-tyrosyl-O-benzyl-L-threonine N-ethyl amide | 6 × 10⁻⁷ | 16.95 | 85 |
| | 3.5 × 10⁻⁷ | 15.31 | 91 |
| | 1 × 10⁻⁷ | 25.65 | 55 |
| | 6 × 10⁻⁸ | 27.03 | 50 |
| | 3.5 × 10⁻⁸ | 28.85 | 44 |
| LRF control | 3.5 × 10⁻¹⁰ | 41.70 | |
| Saline control | | 12.55 | |
| $N^\alpha$-cyclohexylcarbonyl-$N^{im}$-benzyl-L-histidyl-O-benzyl- | 1 × 10⁻⁶ | 8.31 | 88 |
| | 5 × 10⁻⁷ | 11.48 | 75 |

-continued

| ACTIVITY TABLE FOR IN VITRO TEST IN RAT ANTERIOR PITUITARY CELL CULTURES | | | |
|---|---|---|---|
| | Molar Conc. | LH Value ng/ml. | % LH Release Inhibition |
| L-tyrosyl-O-benzyl-L-threonine methyl ester | | | |
| LRF control | $3.5 \times 10^{-10}$ | 29.67 | |
| Saline control | | 5.38 | |

The luteinizing hormone releasing factor (LRF) is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. (For a report of the structure of LRF, which has also been referred to as luteinizing hormone releasing hormone, or LH-RH, and its biological activity, see Science, Vol. 174, No. 4008, Oct. 29, 1971, pages 511–512. Thus, the tripeptides of this invention are useful in controlling ovulation and in restricting fertility.

The invention is illustrated by the following examples.

EXAMPLE 1

$N^\alpha$-t-Butoxycarbonyl-$N^{im}$-benzyl-L-histidyl-O-benzyl-L-tyrosyl-O-benzyl-L-threonine methyl ester The methyl ester is obtained by stirring 5.6 g. of $N^\alpha$-t-butoxycarbonyl-$N^{im}$-benzyl-L-histidyl-O-benzyl-L-tyrosyl-O-benzyl-L-threonine resin in 200 ml. of methanol and 20 ml. of triethylamine for 2 days. The solvent is evaporated and the residue is chromatographed on silica gel using methanol-benzene (1:4) to yield 1.1 g. as a mono-hydrate; m.p. 48°–52° C.

$N^\alpha$-t-Butoxycarbonyl-$N^{im}$-benzyl-L-histidyl-O-benzyl-L-tyrosyl-O-benzyl-L-threonine resin is obtained by the following procedure.

A tubular flask of 400 ml. capacity, having a sintered glass disc and stopcock at one end and a suitably placed opening for addition of materials at the other is clamped to a motor which imparts a rocking motion to the flask. The flask is charged with (20.3 g.) of $N^\alpha$-t-butoxycarbonyl-O-benzyl-L-threonine resin and 200 ml. of dichloromethane and agitated for one half hour. The liquid is then drained from the flask by connecting a suction, through a trap, to the stopcock. The resin is retained in the flask by means of the sintered glass disc. The $N^\alpha$-t-butoxycarbonyl protecting group is removed by rocking the resin with 100 ml. of trifluoroacetic acid and 100 ml. of dichloromethane for ten minutes. The liquid is drained from the flask and the trifluoroacetate O-benzyl-L-threonine resin is washed five times with 200 ml. of dichloromethane each time. The trifluoroacetate salt of O-benzyl-L-threonine resin is converted to O-benzyl-L-threonine resin by the addition of 20 ml. of triethylamine in 200 ml. of cold dichloromethane and rocking the reaction for 10 minutes. The flask is drained and the resin again washed five times with 200 ml. of dichloromethane each time. The O-benzyl-L-tyrosine moiety is coupled to the O-benzyl-L-threonine resin by adding 6.7 g. of $N^\alpha$-t-butoxycarbonyl-O-benzyl-L-tyrosine in 200 ml. of dichloromethane, shaking for 60 minutes, adding 3.7 g. of dicyclohexylcarbodiimide in 50 ml. of dichloromethane and rocking the reaction flask for 24 hours. The flask is drained and the resin washed three times with 200 ml. of dichloromethane each time. Trifluoroacetic acid (100 ml.) and dichloromethane (100 ml.) are used as above to remove the t-butoxycarbonyl protecting group from 11.3 g. of the resin and the resin drained and washed as before. Triethylamine, 20 ml. in 200 ml. of cold dichloromethane, is used to remove trifluoroacetic acid and the O-benzyl-L-tyrosyl-O-benzyl-L-threonine resin, is treated with 3.1 g. of $N^\alpha$-t-butoxycarbonyl-$N^{im}$-benzyl-L-histidine in 200 ml. of dichloromethane, rocked for sixty minutes and 1.9 g of dicyclohexylcarbodiimide added in 50 ml. of dichloromethane. The coupling reaction is rocked for 24 hours, the flask drained and the resin washed two times with 200 ml. of dichloromethane each time. The resin is then washed with methanol-chloroform (1:2), three times with 200 ml., with methanol, three times with 200 ml., with ether, three times with 200 ml. and is air dried for 2 hours.

A mixture of 20 g. of chloromethylated polystyrene resin having 1.16 mmole of chlorine per gram, and 8 g. of $N^\alpha$-t-butoxycarbonyl-O-benzyl-L-threonine in 500 ml. of ethanol is treated with 2.6 g. of triethylamine and refluxed for 3 days in excess ethanol. The resin is separated by filtration, washed with ethanol, water, methanol, dichloromethane and ether, successively, and then dried overnight at 40° C. giving the $N^\alpha$-butoxycarbonyl-O-benzyl-L-threonine resin.

The general procedure and equipment for solid phase peptide synthesis is described by Stewart and Young, "Solid Phase Peptide Synthesis", W. H. Freeman and Company, San Francisco, 1969.

EXAMPLE 2

$N^\alpha$-t-Butoxycarbonyl-$N^{im}$-benzyl-L-histidyl-O-benzyl-L-tyrosyl-O-benzyl-L-threonine N-ethylamide $N^\alpha$-t-Butoxycarbonyl-$N^{im}$-benzyl-L-histidyl-O-benzyl-L-tyrosyl-O-benzyl-L-threonine methyl ester, 0.3 g., is dissolved in anhydrous methanol, 150 ml., and treated with an excess, 10 ml., of ethylamine. The reaction is let stand at room temperature for 2 days and worked up by evaporating the solvent and chromatographing the residue on silica gel with methanol-chloroform (3:7) to yield 0.2 g. as a hemihydrate; m.p. 70°–75° C.

EXAMPLE 3

$N^\alpha$-Cyclohexylcarbonyl-$N^{im}$-benzyl-L-histidyl-O-benzyl-L-tyrosyl-O-benzyl-L-threonine methyl ester The methyl ester is obtained by stirring 5.0 g. of $N^\alpha$-cyclohexylcarbonyl-$N^{im}$-benzyl-L-histidyl-O-benzyl-L-tyrosyl-O-benzyl-L-threonine resin in 200 ml. of methanol and 20 ml. of triethylamine for 2 days. The solvent is evaporated and the residue is chromatographed on silica gel using methanolbenzene (1:4) to yield 1.3 g. as a hemi-hydrate; m.p. 93°–98° C.

$N^\alpha$-Cyclohexylcarbonyl-$N^{im}$-benzyl-L-histidyl-O-benzyl-L-tyrosyl-O-benzyl-L-threonine resin, 5.0 g., is obtained from 5.6 g. of $N^\alpha$-t-butoxycarbonyl-$N^{im}$-benzyl-L-histidyl-O-benzyl-L-tyrosyl-O-benzyl-L-threonine resin by washing the resin two times with 200 ml. of dichloromethane, deblocking with 200 ml. of 50% trifluoroacetic acid in dichloromethane for 10 minutes, washing with 200 ml. of dichloromethane five times; neutralizing with 200 ml. of 10% triethylamine in dichloromethane for 10 minutes, washing with 200 ml. of dichloromethane five times; adding 0.64 g. of cyclohexylcarboxylic acid (hexahydrobenzoic acid) and equilibrating with 200 ml. of dichloromethane during one hour; adding 1.1 g. of dicyclohexylcarbodiimide in 20 ml. of dichloromethane and agitating the reaction overnight. The resin is drained and washed with 200 ml. of dichloromethane five times.

EXAMPLE 4

$N^\alpha$-t-Butoxycarbonyl-$N^{im}$-benzyl-L-histidyl-O-benzyl-L-tyrosyl-O-benzyl-L-threonine amide The dried tripeptide resin (Example 1) is added to a cold 10° C solution of 150 ml. of methanol saturated with gaseous ammonia. The flask is tightly stoppered and the mixture is stirred for two days at room temperature. The flask is then cooled, opened, and the mixture filtered. The resin is washed with 50 ml. of hot dimethylformamide and the combined filtrate is evaporated and ether added yielding the tripeptide amide.

EXAMPLE 5

$N^\alpha$-Cyclohexylcarbonyl-$N^{im}$-benzyl-L-histidyl-O-benzyl-L-tyrosyl-O-benzyl-L-threonine N-ethylamide $N^\alpha$-Cyclohexylcarbonyl-$N^{im}$-benzyl-L-histidyl-O-benzyl-L-tyrosyl-O-benzyl-L-threonine methyl ester, 0.3 g., is dissolved in anhydrous methanol, 200 ml., and treated with an excess, 10 ml., of ethylamine. The reaction is let stand at room temperature for 2 days and worked up by evaporating the solvent and chromatographing the residue on silica gel with 10% methanol in benzene to yield 0.2 g. as a monohydrate; m.p. 155°–160° C.

I claim:
1. A tripeptide represented by the formula

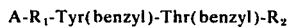

wherein $A$ is t-butoxycarbonyl or cyclohexylcarbonyl, $R_1$ is Trp, His(benzyl), Cys(benzyl) or Pro and $R_2$ is lower alkoxy, hydrazino, amino, lower alkylamino, di(lower alkyl)amino, benzylamino, allylamino, (diethoxyphosphinyl)methylamino, 2-(diethoxyphosphinyl)ethylamino or 2-[[(phenylmethyl)amino]sulfonyl]ethylamino.

2. The compound of claim 1 having the name $N^\alpha$-t-butoxycarbonyl-$N^{im}$-benzyl-L-histidyl-O-benzyl-L-tyrosyl-O-benzyl-L-threonine N-ethylamide.

* * * * *